(12) United States Patent
Zavracky

(10) Patent No.: US 6,320,568 B1
(45) Date of Patent: Nov. 20, 2001

(54) CONTROL SYSTEM FOR DISPLAY PANELS

(75) Inventor: Matthew Zavracky, North Attleboro, MA (US)

(73) Assignee: Kopin Corporation, Taunton, MA (US)

( * ) Notice: Subject to any disclaimer, the term of this patent is extended or adjusted under 35 U.S.C. 154(b) by 0 days.

(21) Appl. No.: 08/364,070

(22) Filed: Dec. 27, 1994

Related U.S. Application Data

(63) Continuation of application No. 07/971,399, filed on Nov. 4, 1992, now abandoned, which is a continuation-in-part of application No. 07/944,207, filed on Sep. 11, 1992, now Pat. No. 5,444,557, which is a continuation-in-part of application No. 07/823,858, filed on Jan. 22, 1992, now abandoned, and a continuation-in-part of application No. 07/872,297, filed on Apr. 22, 1992, now Pat. No. 5,317,436, which is a continuation-in-part of application No. 07/839,241, filed on Feb. 20, 1992, now abandoned, which is a continuation-in-part of application No. 07/636,602, filed on Dec. 31, 1990, now Pat. No. 5,206,749.

(51) Int. Cl.[7] .................................... G09G 3/36

(52) U.S. Cl. ................ 345/101; 345/96; 345/90

(58) Field of Search ............... 345/98, 99, 100, 345/87, 89, 93, 96, 101, 102, 103, 207, 205, 204, 209; 359/54, 55; 348/792; 349/72

(56) References Cited

U.S. PATENT DOCUMENTS

| | | | |
|---|---|---|---|
| 4,024,626 | 5/1977 | Leupp et al. | 29/571 |
| 4,393,380 | 7/1983 | Hosokawa et al. | 345/90 |
| 4,429,305 | 1/1984 | Hosokawa et al. | 345/90 |
| 4,582,395 | 4/1986 | Morozumi | 359/57 |
| 4,583,122 | * 4/1986 | Ohawada et al. | 345/792 |
| 4,600,274 | 7/1986 | Morozumi | 359/58 |
| 4,634,225 | 1/1987 | Haim et al. | 349/161 |

(List continued on next page.)

FOREIGN PATENT DOCUMENTS

| | | |
|---|---|---|
| 0151508 | 8/1985 | (EP) . |
| 0 241 562 | 10/1987 | (EP) . |
| 0 313 331 | 4/1989 | (EP) . |
| 0 352 636 | 1/1990 | (EP) . |
| 63055529 | 10/1988 | (JP) . |
| 1038727 | 9/1989 | (JP) . |
| 1280795 | 11/1989 | (JP) . |
| 2216120 | 8/1990 | (JP) . |
| 3096918 | 7/1991 | (JP) . |
| 62271569 | 11/1997 | (JP) . |
| 93/15589 | 8/1993 | (WO) . |

OTHER PUBLICATIONS

Yamano et al. "The 5–Inch Size Full Clor Liquid Crystal Television Addressed By Amorphous Silicon Thin Film Transistors" IEEE Transactions of Consumer Electronics, CE–31 No. 1 (Feb. 1985), pp. 39–46.

*Primary Examiner*—Xiao Wu
(74) *Attorney, Agent, or Firm*—Hamilton, Brook, Smith & Reynolds, P.C.

(57) ABSTRACT

A control apparatus for an active matrix liquid crystal display device is fabricated with the active matrix as a single integrated SOI circuit. The control apparatus and the active matrix are lifted from a silicon substrate and transferred to a glass substrate as a single piece. The control apparatus comprises a video interface, a column driver, and dual row drivers. The video interface operates the active matrix as a multiple-frequency scanning display device. The column driver comprises dual shift register arrays, one array coupled to the even columns and the other array coupled to the odd columns. The even and odd columns operate at opposite polarities. The respective polarities are reversed on every frame by a polarity switch the polarity switch coupled to a video signal amplifier. The control apparatus further comprises sensors for generating a gray-scale feedback signal to adjust the amplifier gain. The sensors comprise a temperature sensor within the active matrix and a light sensor measuring light transmission through the liquid crystal material.

38 Claims, 12 Drawing Sheets

U.S. PATENT DOCUMENTS

| | | | |
|---|---|---|---|
| 4,653,862 | 3/1987 | Morozumi | 359/58 |
| 4,655,551 | 4/1987 | Washizuka et al. | 359/83 |
| 4,716,403 | 12/1987 | Morozumi | 345/88 |
| 4,740,782 | 4/1988 | Aoki et al. | 345/92 |
| 4,779,085 * | 10/1988 | Mizutome | 345/205 |
| 4,807,974 | 2/1989 | Hirai | 359/54 |
| 4,808,983 | 2/1989 | Benjamin et al. | 345/90 |
| 4,838,654 | 6/1989 | Hamaguchi et al. | 359/59 |
| 4,842,371 * | 6/1989 | Yasuda et al. | 345/103 |
| 4,859,997 | 8/1989 | Bouron et al. | 345/59 |
| 4,886,343 | 12/1989 | Johnson | 359/53 |
| 4,888,599 * | 12/1989 | Harwood et al. | 345/101 |
| 4,917,468 | 4/1990 | Matsuhashi et al. | 359/55 |
| 4,917,469 * | 4/1990 | Ross | 345/101 |
| 4,923,285 | 5/1990 | Ogino et al. | 345/101 |
| 4,952,031 | 8/1990 | Tsunoda et al. | 359/54 |
| 4,952,032 | 8/1990 | Inoue et al. | 345/101 |
| 5,032,007 | 7/1991 | Silverstein et al. | 359/53 |
| 5,088,806 * | 2/1992 | McCartney et al. | 345/101 |
| 5,093,655 * | 3/1992 | Tanioka | 345/96 |
| 5,095,304 | 3/1992 | Young | 345/92 |
| 5,115,229 * | 5/1992 | Shalit | 345/207 |
| 5,115,232 | 5/1992 | Iizuka | 345/213 |
| 5,117,298 | 5/1992 | Hirai | 359/55 |
| 5,206,749 | 4/1993 | Zavracky et al. | 359/59 |
| 5,247,378 * | 9/1993 | Miller | 349/72 |
| 5,347,154 | 9/1994 | Takahashi et al. | 257/347 |

* cited by examiner

CONTROL SYSTEM FOR DISPLAY PANELS

RELATED APPLICATION

This application is a continuation of application Ser. No. 07/971,399 filed Nov. 4, 1992, now abandoned which is a Continuation-In-Part of U.S. patent application Ser. No. 07/944,207 filed on Sep. 11, 1992, now U.S. Pat. No. 5,444,557, which is also a Continuation-In-Part of U.S. patent application Ser. No. 07/823,858 filed on Jan. 22, 1992, now abandoned, and of Ser. No. 07/872,297 filed Apr. 22, 1992, now U.S. Pat. No. 5,317,436 which is a Continuation-In-Part of U.S. patent application Ser. No. 07/839,241 filed Feb. 20, 1992, now abandoned, which is a Continuation-In-Part of U.S. patent application Ser. No. 07/636,602 filed Dec. 31, 1990 now U.S. Pat. No. 5,206,799.

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCDs generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across it between the circuit panel and a ground affixed to the filter plates. Thus, when a particular pixel of the display is turned on, the liquid crystal material rotates polarized light being transmitted through the material so that it will pass through the second polarizing filter.

The primary approach to TFT formation over the large areas required for flat panel displays has involved the use of amorphous silicon which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass which generally restricts further circuit processing to low temperatures.

A continuing, need exists for systems and methods of controlling pixel of a panel displays having the desired speed and providing for ease, and reduced cost, of fabrication.

SUMMARY

The invention is a control system for a liquid crystal display panel. A control apparatus is fabricated with the active matrix as a monolithic SOI structure. After the SOI structure is fabricated on a silicon substrate, the structure is removed from the silicon substrate using a lift-off process and transferred to a glass substrate as a single substrate. The single structure provides improved processing speeds and the fabrication process reduces the difficulty and cost of manufacturing display panels.

In a preferred embodiment, a control apparatus for a liquid crystal display device comprises a video interface, a left select scanner, a right select scanner, a video polarity switch, and a data scanner. The video interface converts video signals from a video source into active matrix control signals. In response to the active matrix control signals, the left and right select scanners simultaneously drive opposite sides of the matrix select lines. The video polarity switch generate an even column video signal and an odd column video signal from the video source signal, the even column signal being of the opposite polarity of the odd column signal. The polarities of the even and the odd column signals are reversed on each sequential video frame. In response to the active matrix control signals, the data scanner drives the active matrix columns with the even and the odd column signals.

The data scanner comprises an odd column shift register array and an even-column shift register array. The odd column array driving the odd columns of the active-matrix and the even column array driving the even columns of the active matrix.

An encoder may be coupled between the video source and the video polarity switch. The encoder generating a superposed analog video signal from a video source RGB data signal. The RGB data signal may be mapped to a superposed color analog signal. The RGB data signal may also be mapped to a gray-scale analog signal. Preferably, the encoder may map to either of the color or gray-scale signal in response to a control signal.

In a preferred embodiments, the control apparatus adjusts the gray-scale video signal level to compensate for changes in the transmittance of the liquid crystal material. A sensor is fabricated within the SOI structure. The sensor generates a data signal in response to the temperature of the active matrix and the light transmittance of the liquid crystal material. The sensor data is processed by a measurer, which generates a feedback signal in response to the sensor data. An amplifier gain is adjusted by the feedback signal, the amplifier amplifying the video signal by the gain. The gain may be linear or nonlinear. The sensor may comprise at least one real-time light sensor and at least one real-time temperature sensor. At least one other light sensor is provided that generates a signal representing light transmittance through a black pixel. The black pixel signal may be generated by permanently grounding the black pixel light sensor. At least one other light sensor is provided that generates a signal representing light transmittance through a white pixel. The white pixel signal may be generated by permanently connecting the white pixel light sensor to a DC voltage. The black and white pixel light sensors define the end points of the active matrix transmittance curve.

In a preferred embodiment, the video source generates a video signal having variable synchronization frequencies. The active matrix display has a fixed pixel resolution. The video interface generates a dot clock signal from the variable synchronization frequencies for driving the display at the fixed resolution. The video interface allows the display panel to function as a multiple-frequency scanning display device.

The video interface comprises a control processor and dot clock regenerator. The control processor is responsive to video mode changes on the video signal as reflected by the synchronization frequencies. In response to mode changes, the control processor signals the dot clock regenerator. The dot clock regenerator is responsive to the control processor signal. The dot clock regenerator comprises a digitally programmable phase-locked loop that tracks changes on the synchronization frequencies such that the dot clock signal is centered over the correct pixel and does not drift. The video interface providing compatibility with VGA and XVGA adapters.

BRIEF DESCRIPTION OF THE DRAWINGS

The above, and other features of the invention including various novel details of construction and combination of parts, will now be more particularly described with reference to the accompanying drawings. It will be understood that the particular display device and the methods used in fabricating the display device which embody the invention are shown by way of illustration only and not as a limitation of the invention. The principle features of this invention can be employed in various embodiments without departing from the scope of the invention.

DETAILED DESCRIPTION OF THE INVENTION

Figure 1:
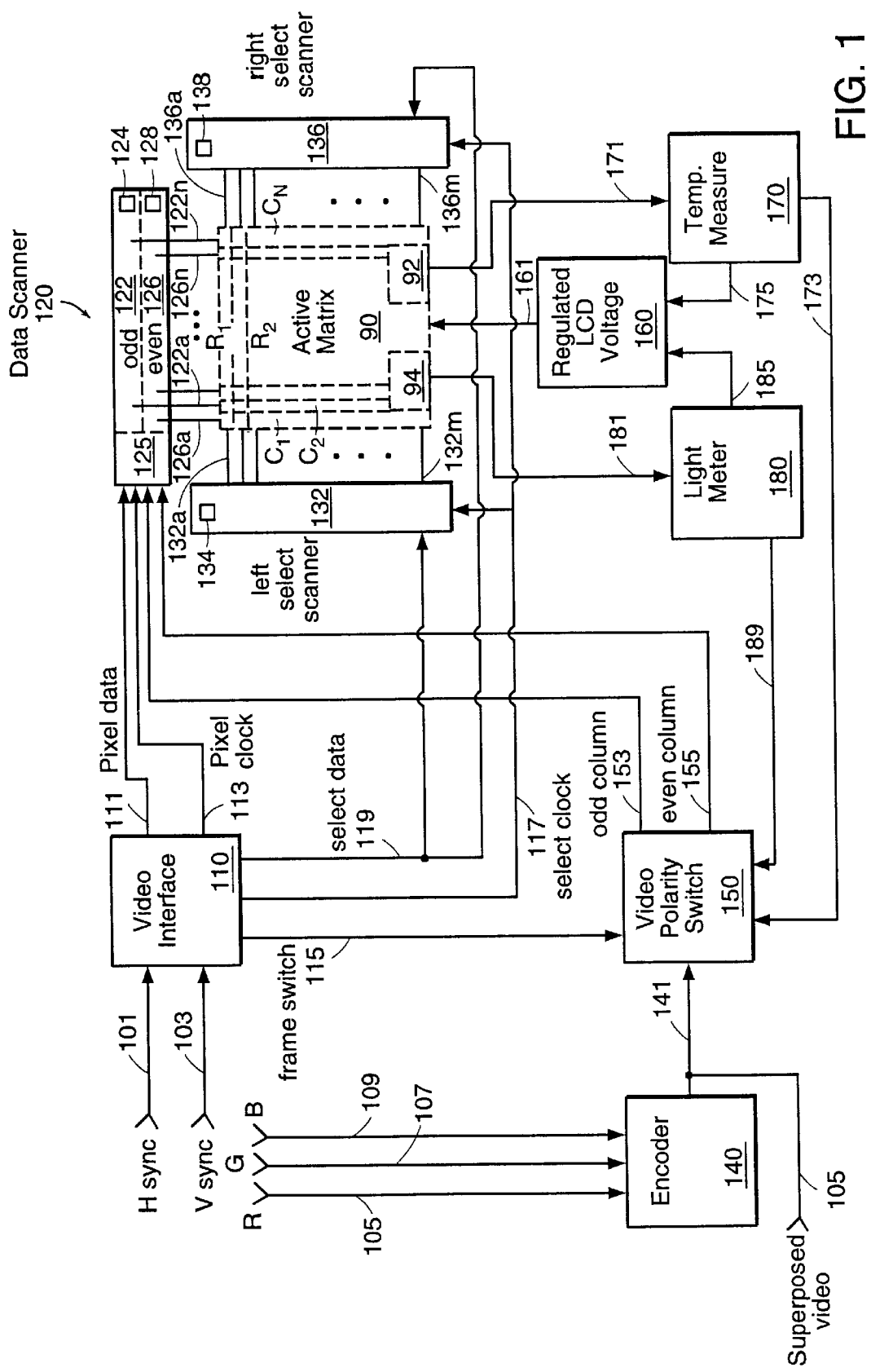
FIG. 1 is a schematic block diagram of a preferred embodiment of the invention.

A preferred embodiment is shown in FIG. 1. A video signal source (not shown) provides video signals to an active matrix display device (shown in phantom). The video signal source can be any analog or digital video signal source including a Video Graphics Array (VGA) adaptor, National Television Systems Committee (NTSC) composite video source, high-resolution professional display adapters, Charge-Coupled-Devices (CCD), or other similar sources. Horizontal and vertical synchronization signals from the video signal source are provided to a video interface 110 on data lines 101 and 103, respectively. Red-Green-Blue (RGB) video signal components, if supplied by the video signal source, are provided to an encoder 140 on respective data lines 105,107,109. If discrete red, green and blue signals are not supplied by the video source (e.g., NTSC composite video signal), then a single video signal must be supplied by the video source. The appropriate video signal is supplied to a video polarity switch 150 on data line 141, the operation of which is described in greater detail below.

The active matrix 90 (shown in phantom) operates as a multi-frequency display device. Typically, video signals from the video signal source will not be synchronized to a fixed frequency. For example, a VGA adaptor generates synchronization signals that vary depending on the particular video mode in which the adaptor is operating. A standard VGA adaptor may generate a vertical synchronization frequency between about 56 and 70 Hz and a horizontal synchronization frequency between about 15 and 35 kHz. For professional display purposes (e.g., CAD/CAM) the vertical and horizontal synchronization frequency may be higher than described. To handle current high resolution displays, the display device must adapt to vertical synchronization frequencies up to about 100 Hz and horizontal synchronization frequencies up to about 66 kHz. Consequently, the display device adapts to changes in the synchronization frequencies.

The video interface 110 is used to interface the active matrix display device with the horizontal and vertical synchronization signals from the video signal source. In a preferred embodiment, the video interface 110 interfaces with a standard VGA display adapter to display the video image at a horizontal resolution of 640 pixels and a vertical resolution of 480 pixels (640 H×480V). In another preferred embodiment, the display resolution is 1024 H×768V. In yet another preferred embodiment, the display resolution is 2048 H×2048V. The video interface 110 adjusts to changes in the input synchronization frequencies by detecting frequency or phase changes in the input signals.

Figure 2A:
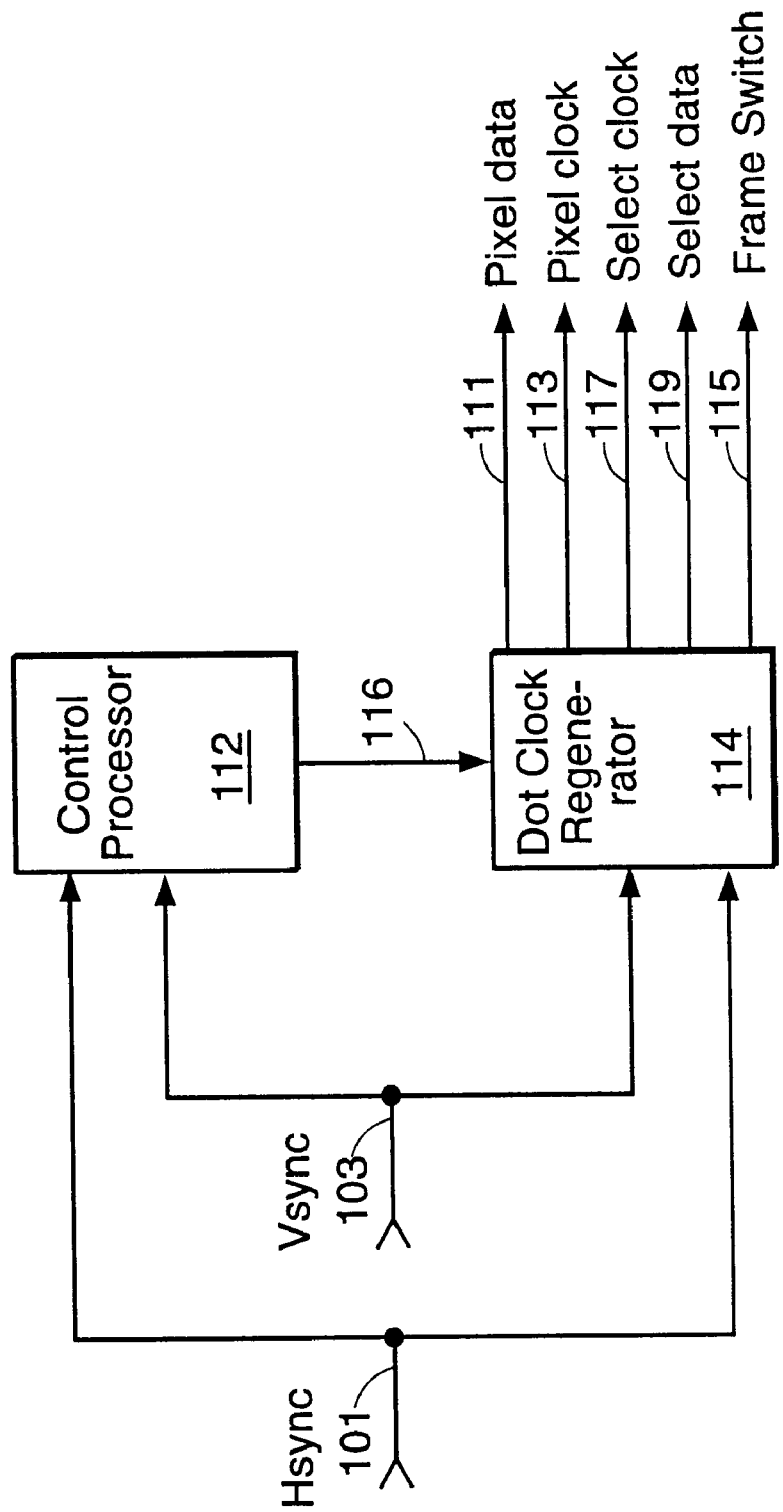
FIGS. 2A–2B are schematic block diagrams of a preferred video interface 110 of FIG. 1.
Figure 2B:
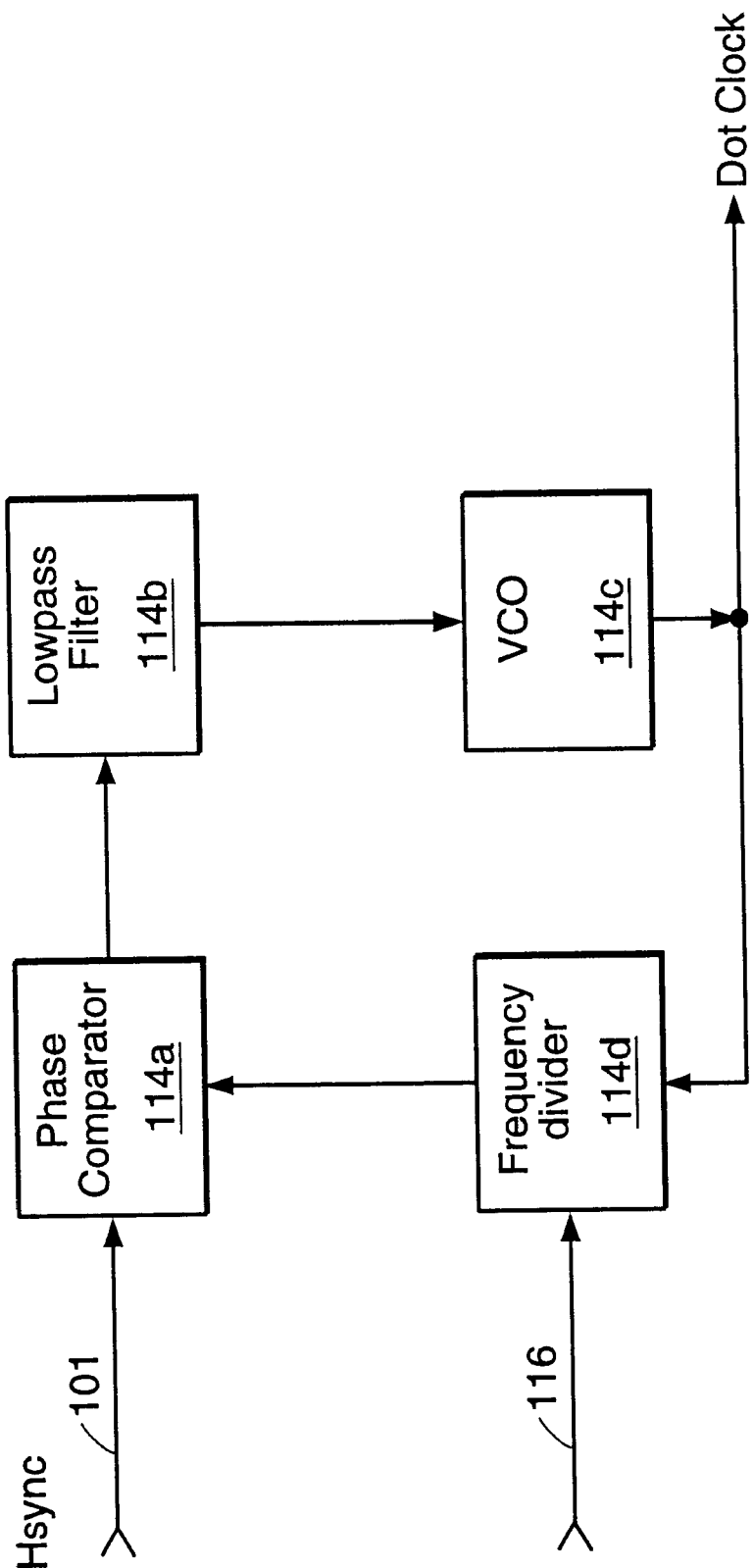

FIGS. 2A–2B are block diagrams of a preferred video interface 110 for VGA signals.

Referring to FIG. 2A, horizontal and vertical synchronization signals are provided at TTL levels on incoming data lines 101,103 from a VGA adapter. A control processor 112 examines the incoming video stream and tracks mode changes, which provide for variable frequency multi-scanning capability. Upon detecting a mode change, the control processor 112 signals the mode change to a dot clock regenerator 114 over data line 116. The dot clock regenerator 114 provides a pixel data signal on line 111, a pixel clock signal on line 113, a frame switch signal on line 115, a select clock signal on line 117, and a select data signal on line 119.

As illustrated in FIG. 2B, the dot clock regenerator 114 recreates the pixel dot clock used by a computer to output pixels. The regeneration must be accurately controlled because it is very important to provide a clock that is centered over each pixel and does not drift. The dot clock regenerator 114 includes a phase locked loop (PLL) comprising a phase comparator 114a, a lowpass filter 114b, a voltage controlled oscillator (VCO) 114c, and a digital programmable frequency divider 114d. The frequency divider 114d is responsive to the mode change signal over data line 116. There is no standard for the frequency of the incoming video signal, which can range from 20 MHz to over 30 MHz, depending on the source.

Returning to FIG. 1, the video interface 110 converts the synchronization signals from the video signal source into pixel timing information for the pixel columns and select line timing information for the pixel rows of the active matrix. The video interface 110 provides control registers to adjust and delay the pixel clock, pixel data, select clock, and select data so the image generated by the video source (e.g. VGA) may be precisely mapped to the active matrix 90 pixel resolution (e.g., 640 H×480V). The video interface 110 provides a pixel data signal and a pixel clock signal to a data scanner 120 on respective data lines 111,113. The video interface 110 also provides a select line data signal and a select line clock signal to select scanners 132,136 on respective data lines 117,119. Finally, the video interface 110 provides a frame switch signal to the video polarity switch 150 on data line 115.

The data scanner 120 provides for double storage of pixel data. The data scanner 120 interfaces with the pixel data signal on line 111 and the pixel clock signal on line 113 via interface component 125. In addition, a serial data stream of video is provided to the odd and even column pixels on respective signal lines 153,155. The data scanner 120 uses an odd shift register array 122 and an even shift register array 126 to store data for each scan. The odd shift register array 122 stores data to odd column pixels and even shift register array 126 stores data to even column pixels. To facilitate fabrication testing, an odd test pad 124 is fabricated on the odd shift register array 122 and an even test pad 128 is fabricated on the even shift register array 126.

To reduce signal loss across the active matrix, the select lines are driven from both sides by select scanners 132,136. As viewed in FIG. 1, left select scanner 132 and right select scanner 136 are connected to the select data line 119 and the select clock line 117. The left select scanner 132 provides a select line signal at the end of the select line nearest the lowest-valued pixel column ($C_1$) and right select scanner 136 provides a select line signal at the end of the select line nearest the highest-valued pixel column ($C_N$). Thus, an identical select line signal is supplied at both ends of the select line. To facilitate fabrication testing, a left scanner test pad 134 is fabricated on the left select scanner 132 and a right scanner test pad 138 is fabricated on the right select scanner 136.

The shift registers of the data scanner 120 and the select scanners 132,136 are dynamic shift registers. The dynamic shift registers rely on capacitor storage without leakage. However, dynamic shift registers are susceptible to leakage, especially when they are exposed to the light. Hence, light shields are needed to protect the scanners 120,132,136 from exposure to light.

Encoder 140 may be a gray scale encoder or a color encoder. The RGB signal is provided on signal lines 105, 107,107. The encoder converts the RGB signal into a mapped analog signal. A gray scale encoder employs a colored mapper to convert the RGB signal into a gray scale equivalent. In a preferred embodiment, each color from the RGB signal is weighted and then summed together to form a gray scale signal. The gray scale mapper uses the equation $$V_o = w_R V_R + w_G V_G + w_B V_B, \quad (1)$$

where $V_o$ is the gray scale output signal; $w_R$, $w_G$, and $w_B$ are the respective weighing for the red, green and blue signals; and $V_R$, $V_G$, and $V_B$ are the respective signal strengths for the red, green and blue signals. In a preferred embodiment of the invention, $w_R=0.3$, $w_G=0.59$ and $w_B=0.11$. However, other weighting values may be used. In addition, other mapping techniques may be employed without affecting the scope of the invention (e.g., digital mapping). A color encoder employs a multiplexer to multiplex the RGB signal into a mixed color equivalent. In a preferred embodiment, the encoder 140 provides either one of gray scale or color encoding, as required. The encoded analog signal from either the gray scale mapper or color encoder is provided to the video polarity switch 150 via an encoder line 141.

In a further embodiment, the video source may be an NTSC composite video source. In an NTSC composite video signal, the RGB signals and the synchronization signals are superposed as a single analog video signal. Because the RGB signals are already encoded in a NTSC composite video signal, no separate encoding is necessary. Instead, the superposed RGB data is extracted from the NTSC composite video signal. The superposed RGB data from an NTSC composite video source is provided to the video polarity switch 150 on line 141.

Figure 3:
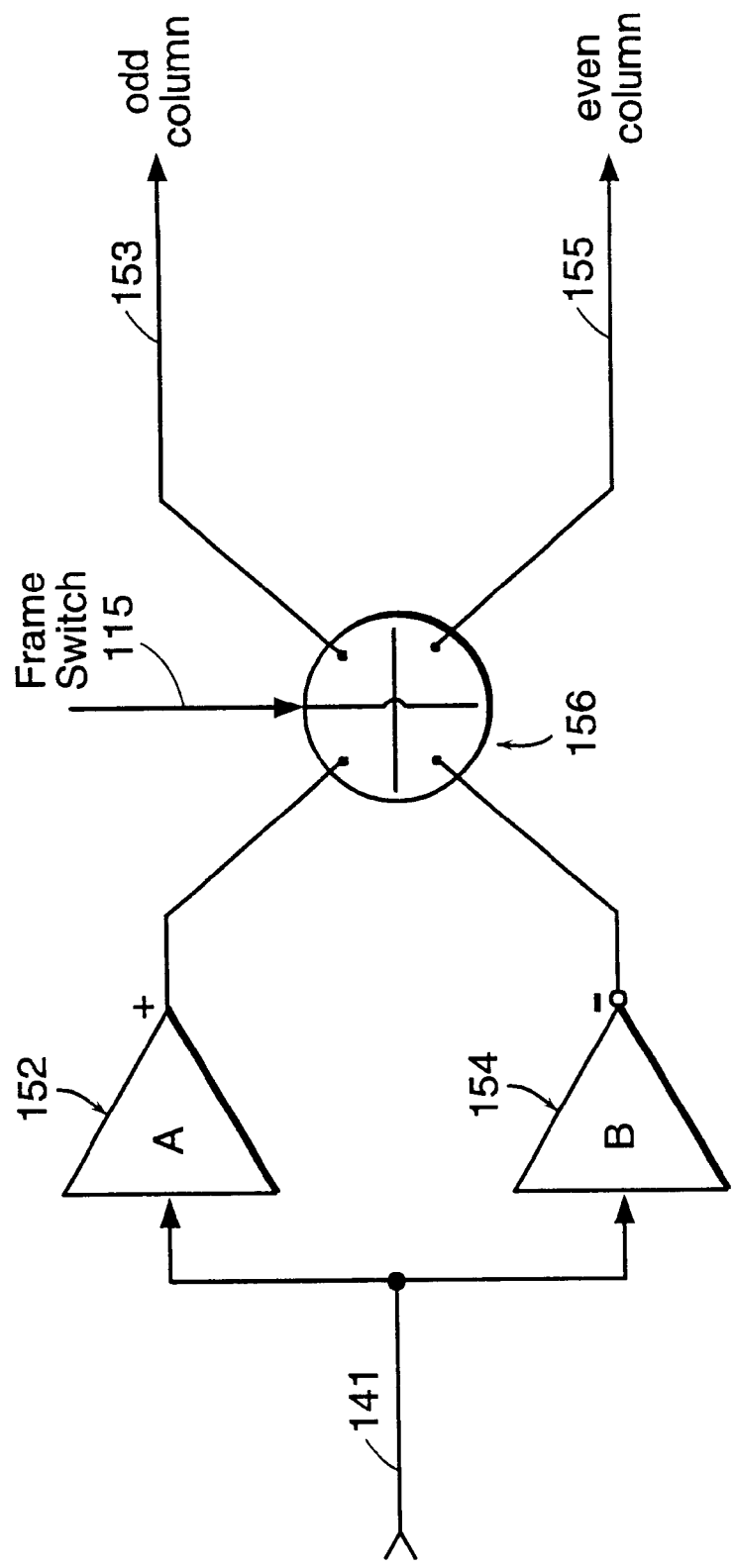
FIG. 3 is a schematic block diagram of a preferred video polarity switch 150 of FIG. 1.

The video polarity switch 150 is driven by the frame switch data on line 115 and the analog video signal on line 141. As shown in FIG. 3, the video polarity switch 150 incorporates amplifiers 152, 154 and an electronic switch 156. The analog video signal from line 141 is provided in parallel to an amplifier 152 having a preselected gain A and to an inverting amplifier 154 having a preselected gain B. Alternatively, the amplifiers' gain may be nonlinear (e.g., gamma functions). The positive and inverted amplifier signals are feed to a switch 156. In a preferred embodiment, the switch 156 is a crossbar switch. The switch 156 is synchronized to the frame rate provided over the frame switch line 115.

A column inversion is used to reduce crosstalk between select lines to reduce or avoid the production of DC offset. The switch 156 provides an alternating opposite polarity for the column pixels. The even column pixels are operated at the opposite polarity of the odd column pixels. The polarities of the column pixels are switched on each sequential frame. For example, on one frame even column pixels operate at a positive polarity and odd column pixels operate at a negative polarity. On the next sequential frame, the switch 156 switches the polarities of the odd and even columns. As a result, the even column pixels operate at a negative polarity and the odd column pixels operate at a positive polarity. The odd column polarity is provided to the active matrix on line 153 and the even column polarity is provided to the active matrix on line 155.

In a further preferred embodiment, at least one sensor is integrated into the active matrix for gray scale adjustments. The sensor may be a temperature diode, a photo transistor or diode, or combinations thereof. Returning to FIG. 1, a preferred embodiment employs at least one temperature sensor 92 and at least one light sensor 94. The signals from the sensors provide feedback signals, to the video polarity switch 150 and the regulated LCD voltage source 160. In response to the feedback signal the polarity switch amplifiers 152, 154 adjust the gray scale signal strength and the regulated LCD voltage source 160 adjusts the LCD voltage.

In a preferred embodiment, the sensors 92,94 are uniformly distributed throughout the active matrix. For example, each pixel element, or a selected group of pixel elements can have an associated sensor 92,94. The sensor to pixel ratio need not be one-to-one however. In an alternative embodiment, the sensors 92,94 are distributed around the perimeter of the active matrix.

Figure 4:
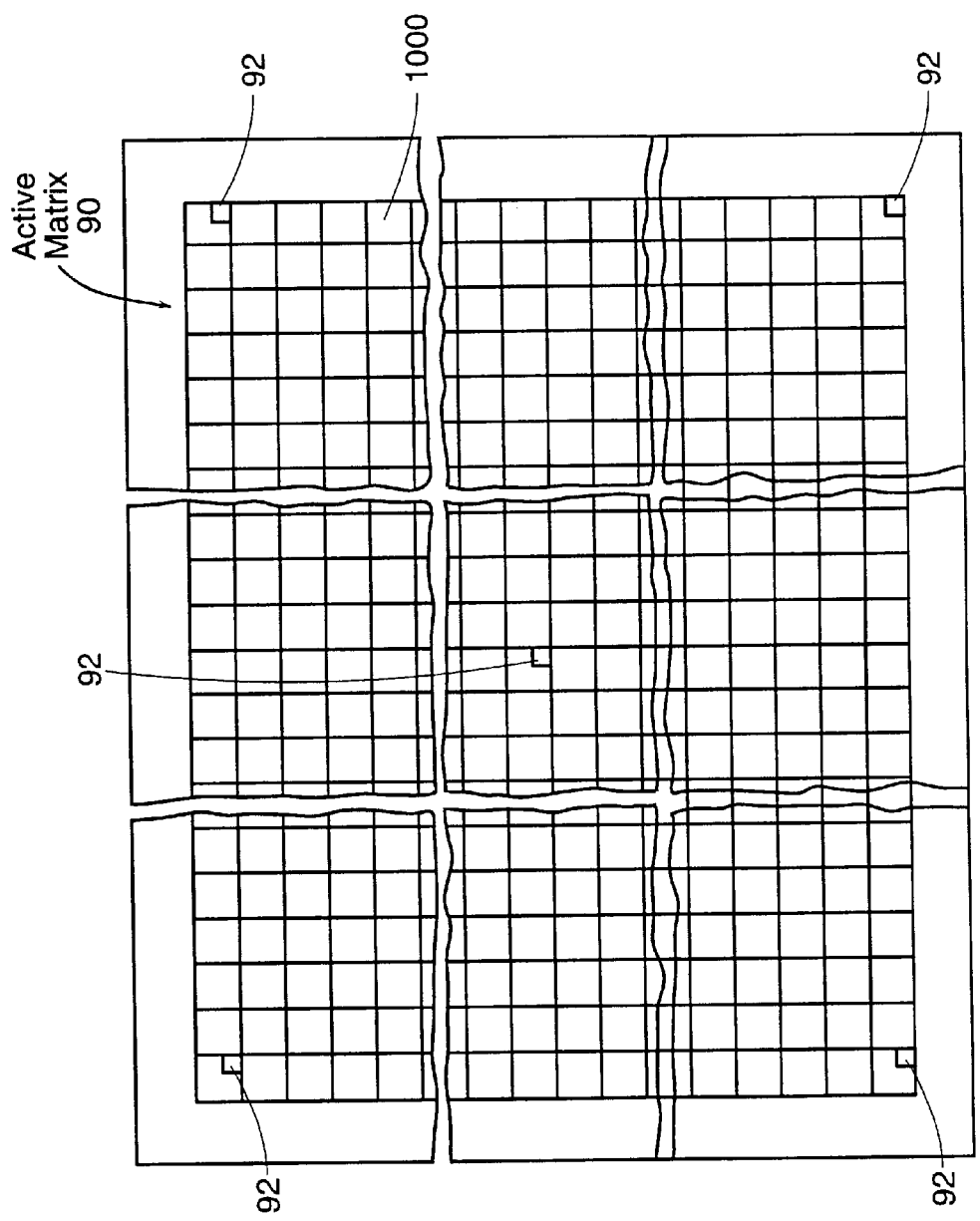
FIG. 4 is a view of the display device showing a preferred temperature sensor arrangement.

FIG. 4 shows a preferred temperature sensor arrangement. The active matrix 90 comprises a plurality of pixels 1000 arranged in columns and rows. Ideally, heat will be absorbed substantially uniformly throughout the liquid crystal material. However, there will be local temperature variations due to the nature of the image being displayed. In the figure, temperature sensors 92 are distributed throughout the active matrix region 90. As shown, temperature sensors 92 are distributed around the perimeter of the active matrix 90. In particular, the temperature sensors 92 are located at corner pixels 1000 of the active matrix 90. In addition, a temperature sensor 92 is disposed near the center of the active matrix 90. Of course, more or less temperature sensors 90 may be used.

Figure 5A:
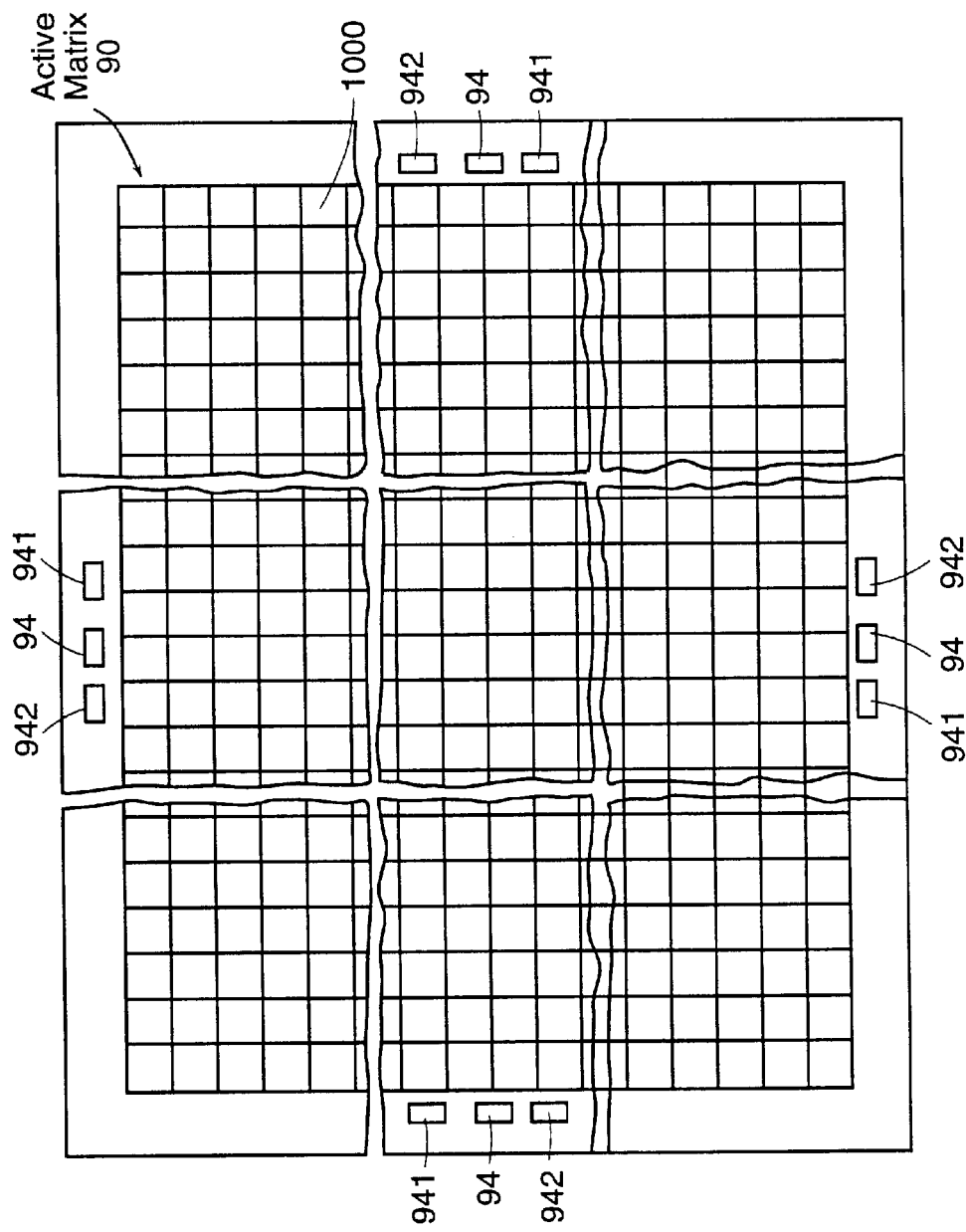
FIGS. 5A–C are views of the display device showing a preferred light sensor arrangement.

FIG. 5A shows a preferred light sensor arrangement. Light sensors are used to construct a transmittance curve for the liquid crystal material. The light sensors 94 are distributed around the active matrix region 94. In addition, there are sensors 941 to indicate a permanently dark pixel reading.

The dark sensors 941 are permanently grounded. There are also sensors 942 that represent permanently white pixel readings by being tied to a DC supply voltage. The permanent-valued sensors 941,942 map the end points of the liquid crystal material's transmittance curve. The light sensor 94 measures the transmission of light through the liquid crystal material in real time. The transmittance of the liquid crystal material varies with the temperature of the material.

Because all light between the polarizes 1095,1089 is polarized, a light sensor 94 located within the active matrix 90 will not measure changes in the transmission of light through the liquid crystal material. To measure changes in the intensity of light, the light transmitted through the liquid crystal material 1081 must be measured after exiting the second polarizer 1089. Although a light sensor may be mounted outside the second polarizer 1089, a preferred embodiment of the invention fabricates the light sensor 94 as part of the SOI circuit 1058.

Figure 5B:
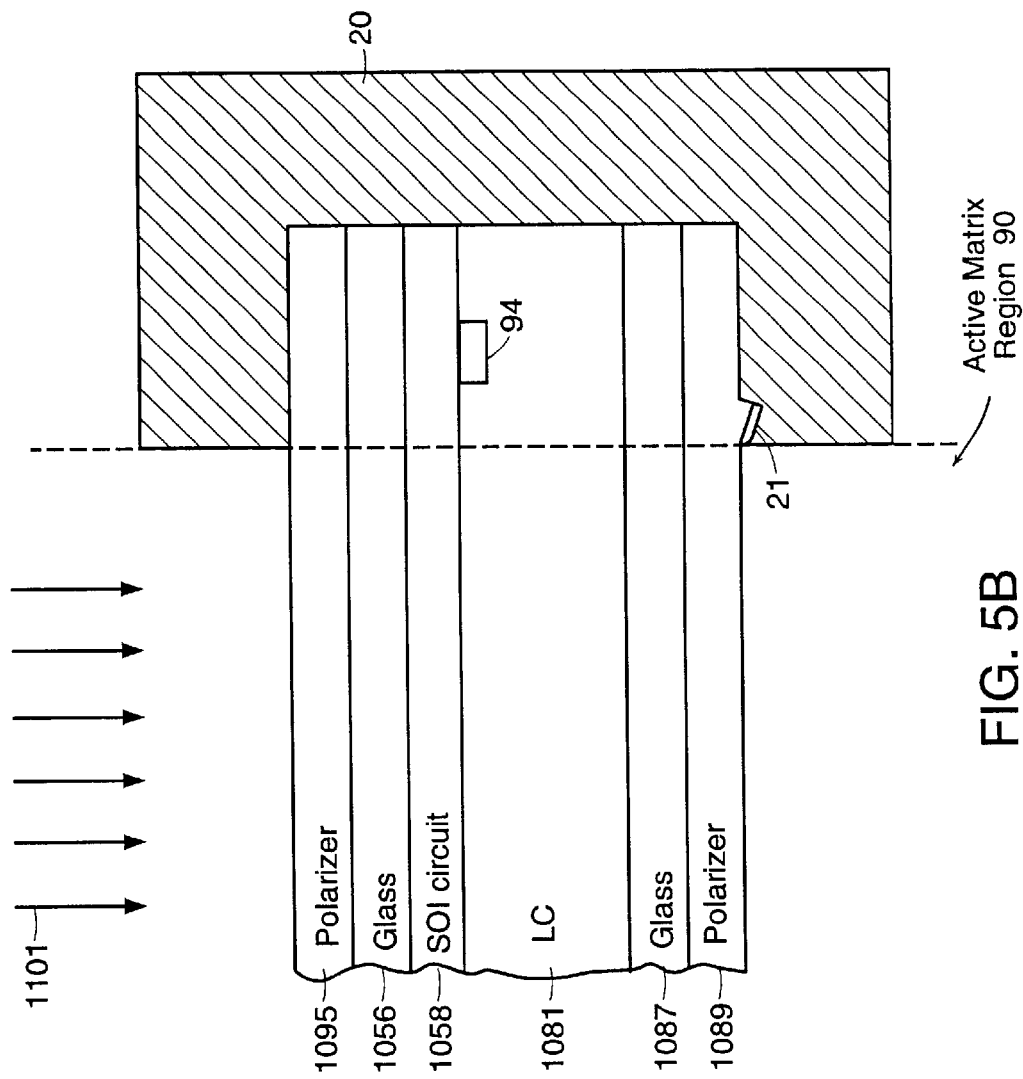
Figure 5C:
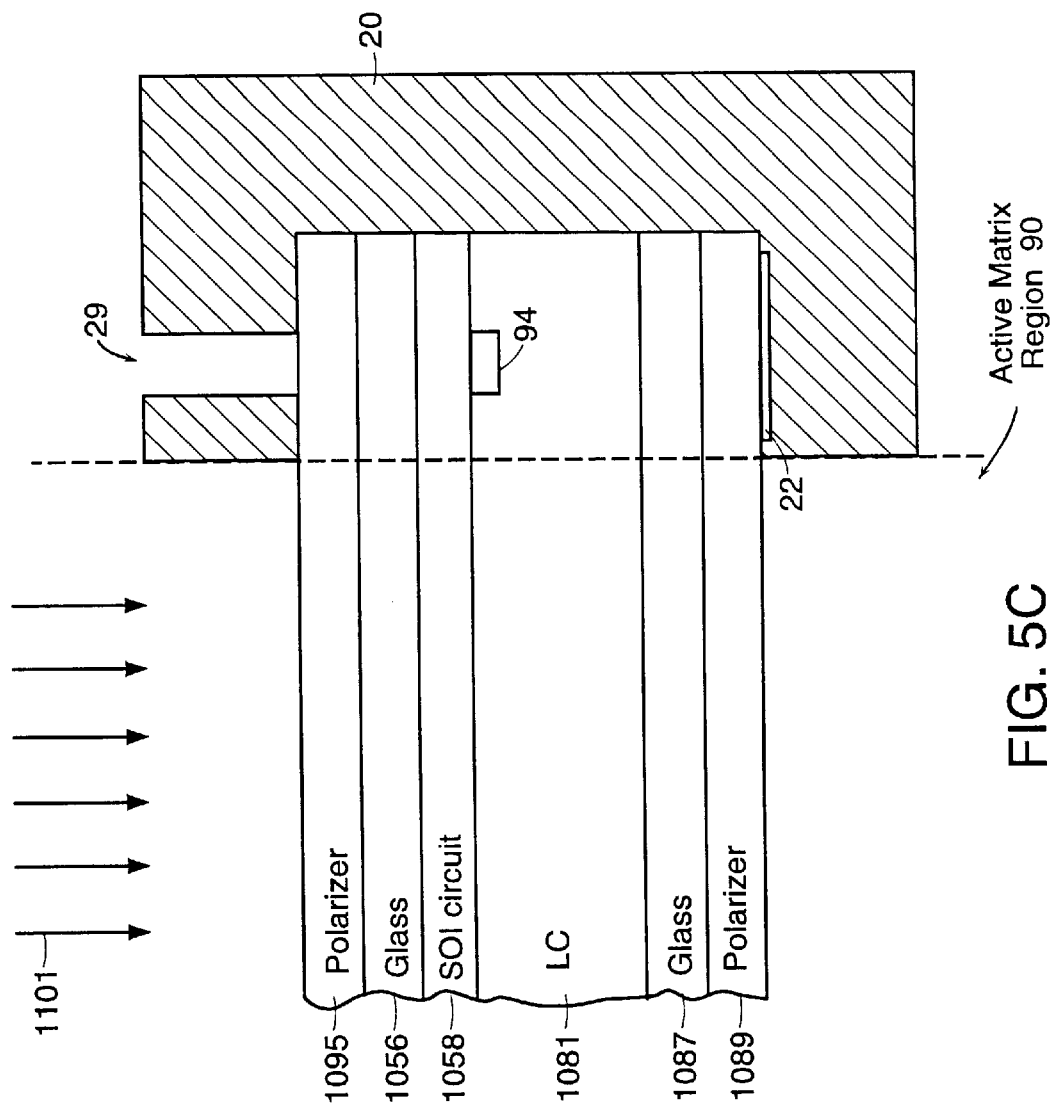

FIGS. 5B–5C are partial cross-sectional views of the display area having a light detector 94. In both figures, the light sensor 94 is located outside of the active matrix region 90. A preferred embodiment is shown in FIG. 5B. A reflector 21 is mounted on a mechanical frame 20. The reflector 21 is inclined such that light that has passed through the liquid crystal material 1081 is reflected toward the light sensor 94. Light sensor 94 is only measuring relative change in light transmission. Therefore, only a minute quantity of light, such as collateral light, needs to be reflected toward the sensor 94.

An alternative embodiment is shown in FIG. 5C, where an aperture 29 is provided through the mechanical frame 20. The incident light 1101 enters the structure through the aperture 29 and passes through the liquid crystal material. After passing through the liquid crystal material, the light 1101 is reflected by a reflector 22 mounted on the mechanical frame 20. The reflected light is thus reflected back to the light sensor 94, where the light intensity is measured. Although the light does not pass through the active matrix region 90, the transmittance can be calculated because the temperature of the liquid crystal material is essentially constant throughout. Therefore, the measurement by light sensor 94 is sufficiently accurate to determine the liquid crystal's relative position on the transmittance curve.

Figure 6A:
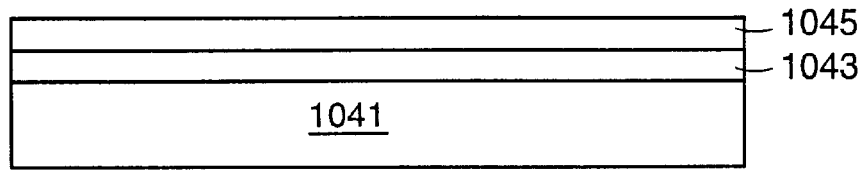
FIGS. 6A–6H illustrate a preferred processed flow sequence illustrating the fabrication of a transmissive active matrix display with a sensor.

FIGS. 6A–6H illustrates a preferred fabrication process for fabricating the sensors 92,94 into the active matrix. Referring to FIG. 6A, an SOI structure includes a silicon substrate 1041 and an insulating oxide layer 1043 (such as, for example, one micron of $SiO_2$) that is grown or deposited on the substrate 1041. A thin (i.e. 0.3 micron) single crystal layer 1045 of silicon is formed over the oxide 1043. The oxide is thus buried beneath the silicon surface layer, such that higher speed devices can be fabricated. However, it is noted that any number of techniques can be employed to provide a thin film of single crystal silicon.

Figure 6B:
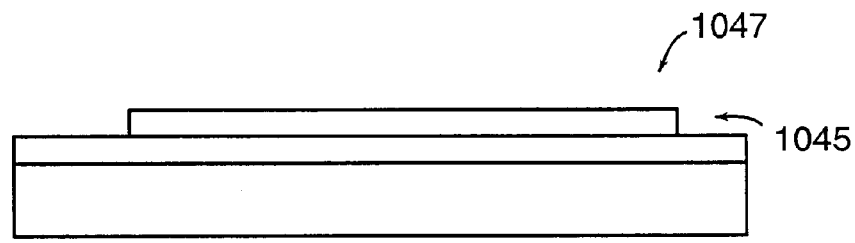
Figure 6C:
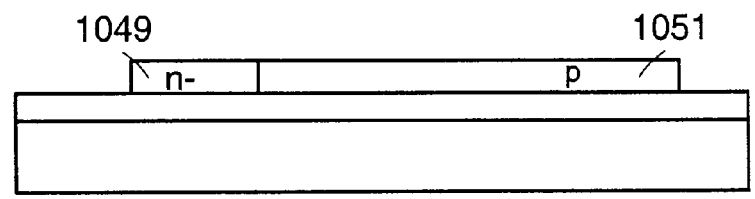

As shown in FIG. 6B, the film 1045 is patterned into islands to define each pixel elements 1047. As explained below, the pixel elements are then processed to form a transistor, an electrode, and sensors 92,94. To that end, the pixel elements are masked (not shown) and subjected to deep and shallow implants to form an n-well region 1049 (FIG. 6C). Another masked is formed over the pixel elements, and the elements are subjected to deep and shallow implants to form an p-well region 1051.

Figure 6D:
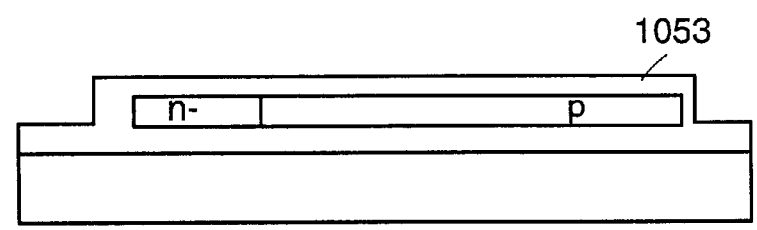
Figure 6E:
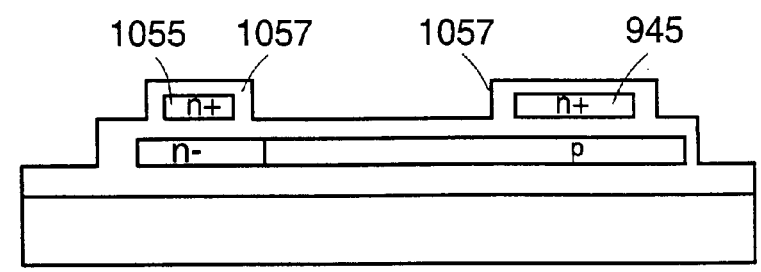

Referring to FIG. 6D, an $SiO_2$ layer 1053 having a thickness on the order of 0.07 micron is formed over each silicon island 1047. A layer of polysilicon having a thickness of about 0.5 micron is formed on the oxide layer 1053, doped to provide an n+ region and patterned to form a transistor gate 1055 and a diode junction 945 (FIG. 6E). Another oxide layer 1057 having a thickness of about 0.07 micron is formed over the polysilicon.

Figure 6F:
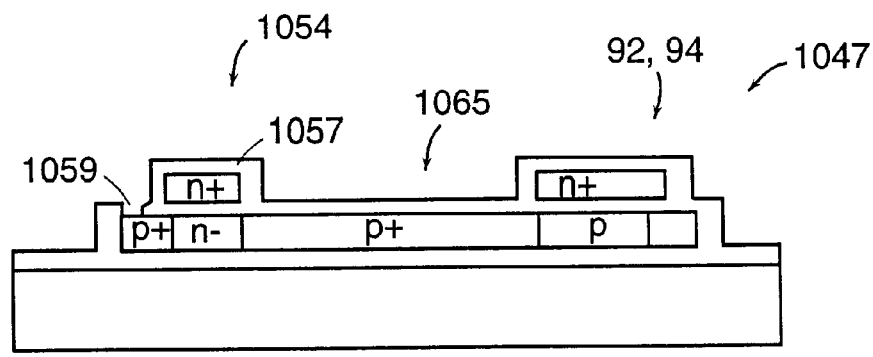

The pixel elements 1047 are masked (not shown) and doped with $2*10^{15}$ of phosphorous to provide an n+ source/drain implantation (FIG. 6F). After the mask is removed, the pixel elements are again masked and doped with $4*10^{15}$ of boron to provide a p+ source/drain implantation. As such, a transistor 1054, a pixel electrode 1065, and a sensor 92, 94 have been formed for pixel element 1047.

Figure 6G:
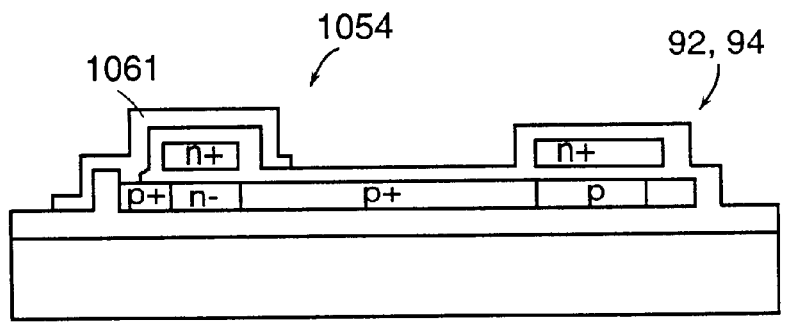

A portion 1059 of the oxide layer is then removed to form a contact for the transistor 1054. Referring to FIG. 6G, a metallization deposition is then performed to form a layer 1061 over the transistor 1054. The layer can comprise aluminum and has a thickness of about one micron. The layer 1061 serves as a pixel light shield as well as a contact for the transistor 1054.

Figure 6H:
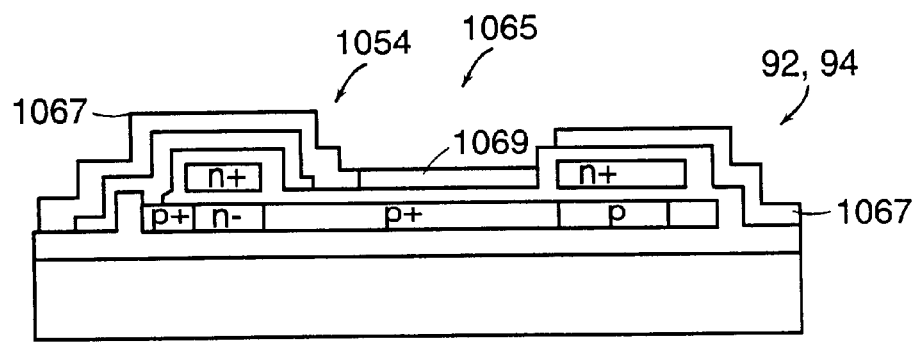

Referring to FIG. 6H, the entire pixel can be coated with a thin (about 0.15 micron) layer of silicon nitride (not shown). Next, a layer of amorphous silicon having a thickness of about 0.5 micron is deposited over each pixel element. The layer is then patterned to provide a matrix of black elements 1067, each black element associated with a transistor. A color filter element 1069 may be formed over the pixel electrode 1065. The color filter elements can be formed by processing an emulsion or a photoresist carrier, or by processing conventional filter materials. The individual color filter elements can be processed to provide an arrangement of three or four different color pixel elements in any of the previously described geometries.

Figure 7:
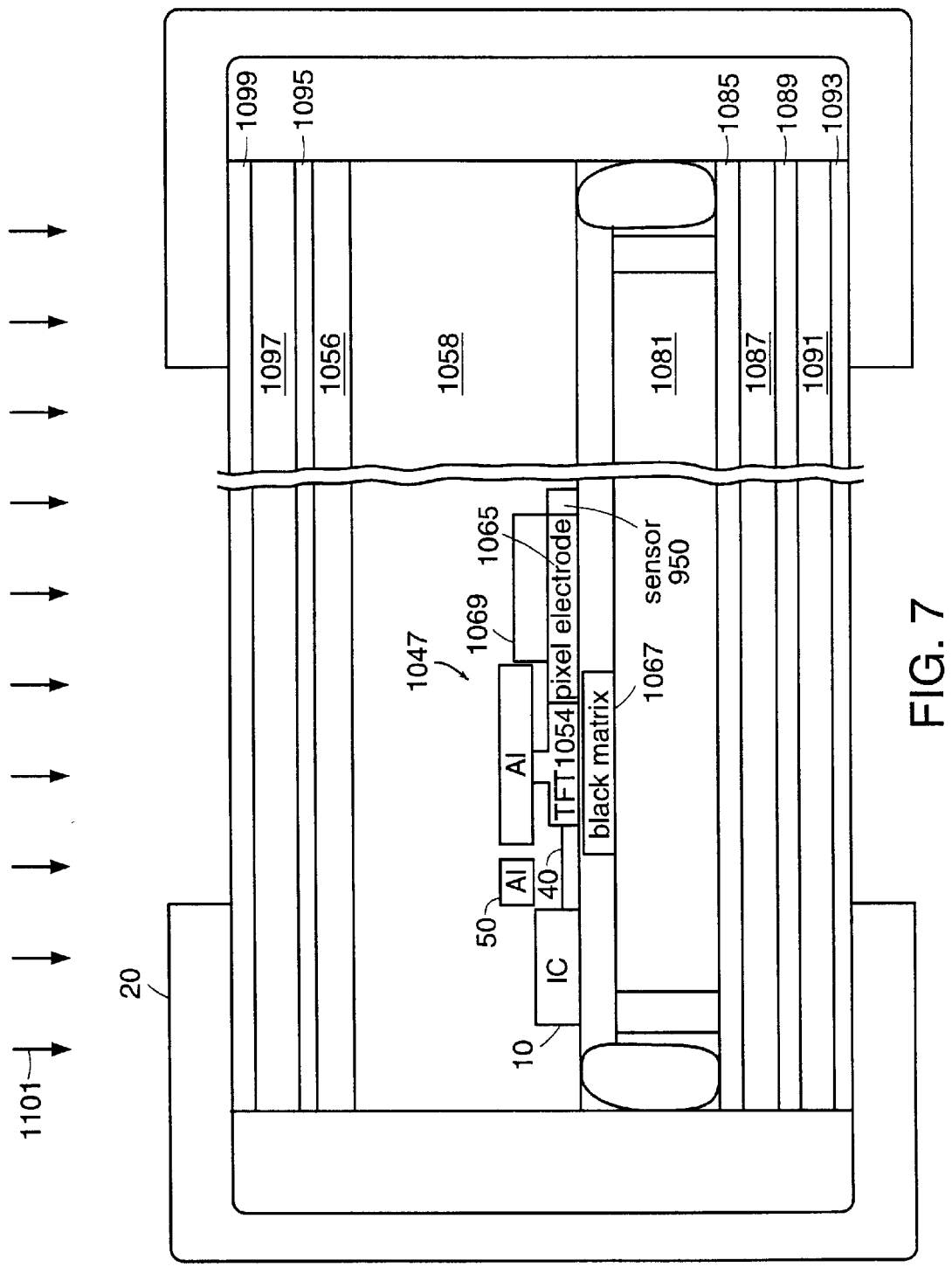
FIG. 7 is a partial cross-sectional view of a preferred active matrix display device.

FIG. 7 shows a partial cross sectional view of a preferred active matrix display device. The display device comprises ITO layers 1093,1099, glass layers 1091,1097 polarizers 1089,1095, cover glass 1087, glass substrate 1056, counter electrode 1085, and liquid crystal 1081.

Integrated into the active matrix is a monolithic integrated circuit 10. In a preferred embodiment, the data scanner 120 and the select scanners 132,136 are integrated onto the integrated circuit 10. In an alternative embodiment, the video interface 110, encoder 140, video polarity switch 150, temperature measurer 170, and light meter 180 are also integrated onto the integrated circuit 10. In addition, a sensor 950 is shown integrated into the active matrix adjacent to the pixel electrode 1065.

For reasons to be explained below, the integrated circuit 10 is connected to the end pixel elements 1047 of each row of pixels by an aluminum interconnect 40. In a preferred embodiment, the aluminum interconnect 40 is 750 microns long.

Because the integrated circuit 10 comprises dynamic shift registers and other optically sensitive components, the integrated circuit 10 must be shielded from exposure to light 1101. A mechanical frame 20 functions to shield the integrated circuit 10 from direct exposure to light 1101. The integrated circuit 10 must be formed far enough away from the active matrix region 90 so the mechanical frame 20 is guaranteed to shield the integrated circuit 10. The distance between the integrated circuit 10 and the active matrix region is dependent on the machined tolerances of the frame 20 and mounting hole, and the tolerance of the glass size. A distance of about 750–1000 microns has been found to be sufficient.

Because of the relatively large distance between the integrated circuit 10 and the active matrix, an interconnect is required. The interconnect 40 must also be shielded from incident light 1101. A metal shield layer 50 formed by metallization disposition functions to shield substantially all of the interconnect 40 from incident light 1101. In a preferred embodiment, the metal shield is formed of aluminum. The aluminum shield 50 also functions to shield the integrated circuit 10 from exposure to collateral directed incident light.

Figure 8:
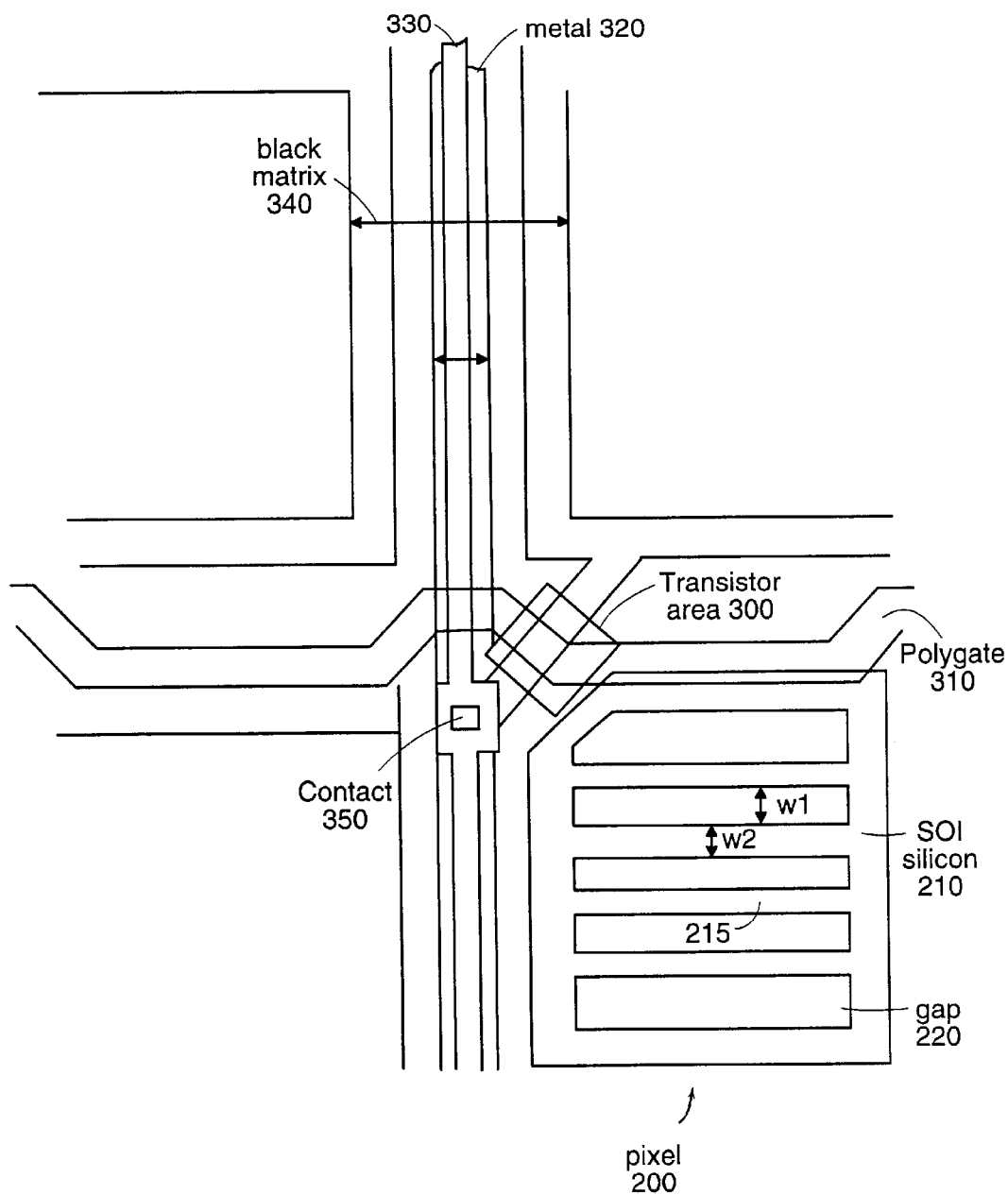
FIG. 8 is a schematic diagram of a patterned pixel electrode.

FIG. 8 is a schematic diagram of a partial pixel array of the active matrix. Generally, four pixel areas 1047 are shown. The silicon material is patterned to form an array of pixel electrodes and each electrode is further patterned into a grid, serpentine, or other suitable geometry to reduce transmission loss through the pixel electrode. The individual pixel electrode 210 initially comprises a solid layer of single crystal silicon. However, the element is processed such that areas 220 of silicon are removed and strips 215 of silicon remain. As such, the resulting pixel electrode 210 resembles a grid. The open areas 220 have a width (W1) of about 6 microns and the strips have a width (W2) of about 3 microns. In a preferred embodiment, there are four strips 215 and five removed areas 220 on the pixel electrode 210.

The grid provides an aperture through each pixel electrode 210 that improves transmission of light by reducing interference effects and also reducing reflection, absorption, and scattering caused by the pixel material. One advantage of the grid-shaped pixels is the increased light transmission through the active matrix, which results in brighter displayed images. Another advantage is that grid-shaped pixels minimize thickness variations in the single crystal silicon layer. These thickness variations cause light absorption or interference, which reduces the light transmission through the active matrix. By minimizing thickness variations, brighter displayed images can be provided.

Equivalents

While this invention has been particularly shown and described with reference and preferred embodiments thereof, it will be understood by those skilled in the art that various changes on form and details may be made therein without departing from the spirit and scope of the invention as defined by the appended claims.

What is claimed is:

1. A control apparatus for driving an active matrix liquid crystal display in response to a stream of video signals from a video source, the display having an array of pixel transistors between a substrate and an opposing substrate, the array being addressed by a plurality of row lines and a plurality of column lines, the apparatus comprising:

an adhesive layer bonding a single crystal silicon layer to the substrate;

a video interface for converting a set of synchronization signals in the video signals to a group of control signals comprising a column control signal, a row control signal, and a polarity control signal;

a first select scanner and a second select scanner disposed within the single crystal silicon layer and coupled to the video interface and responsive to the row control signal, each select scanner coupled to each row line at opposite sides of the active matrix region with each select scanner generating a simultaneous select line drive signal to drive the pixel transistors addressed by the select row line wherein each addressed pixel transistor receives at least a portion of the simultaneous drive signal from each select scanner;

a video polarity circuit coupled to the video source and the video interface and responsive to the polarity control signal, the polarity circuit generating an intensity signal to be applied to the pixel transistors addressed by the select row line, the polarity of the intensity signal being reversed in response to the polarity control signal;

a data scanner disposed within the single crystal silicon layer and coupled to the video interface, the video polarity circuit and the column lines, the data scanner driving the pixel transistors with the intensity signal in response to the column control signal; and a temperature sensor positioned between the substrate and the opposing substrate and formed with the single crystal silicon layer for sensing the temperature of the active matrix liquid crystal display.

2. The control apparatus of claim 1 wherein the data scanner comprises an odd column data scanner for driving the odd columns of the active matrix and an even column data scanner for driving the even columns of the active matrix.

3. The control apparatus of claim 1 further comprising an encoder coupled between the video source and the video polarity circuit, the encoder generating a superposed analog intensity signal from a video source RGB data signal.

4. The control apparatus of claim 3 wherein the encoder maps the RGB data signal to a superposed color analog signal.

5. The control apparatus of claim 3 wherein the encoder maps the RGB data signal to a gray-scale analog signal.

6. The control apparatus of claim 1 further comprising a temperature measurer coupled to the temperature sensor for generating a temperature feedback signal to adjust the intensity signal in response to the temperature data.

7. The control apparatus of claim 6 wherein the video polarity circuitry is coupled to the temperature measurer and comprises an amplifier, a gain of the amplifier being responsive to the temperature feedback signal.

8. The control apparatus of claim 5 further comprising at least one light sensor located between the substrates for signaling relative light transmission changes through the liquid crystal.

9. The control apparatus of claim 8 further comprising a light meter coupled to the light sensor for generating a light feedback signal to adjust the intensity signal in response to the light transmission change.

10. The control apparatus of claim 9 wherein the video polarity circuit is coupled to the light meter and comprises an amplifier, a gain of the amplifier being responsive to the light feedback signal.

11. The control apparatus of claim 1 wherein the video polarity circuit generates an odd column video signal for driving odd columns of the active matrix and an even column video signal for driving even columns of the active matrix, the odd column video signal and the even column video signal being of opposite polarities.

12. The control apparatus of claim 1 wherein the select scanners comprise respective shift registers, the shift registers being shifted to sequentially enable a select row line in response to the row control signal.

13. The control apparatus of claim 1 wherein the video interface comprises a phase-locked loop circuit for tracking changes in the synchronization signals.

14. The control apparatus of claim 1 wherein the active matrix region has at least 640 column lines and at least 480 row lines.

15. The control apparatus of claim 14 wherein the active matrix region has at least 1024 column lines and at least 768 row lines.

16. The control apparatus of claim 1 wherein the device layer is an SOI structure.

17. A control apparatus for adjusting a gray scale video signal of an active matrix liquid crystal display panel, the panel having an active matrix layer fabricated as a single crystal silicon layer of a silicon-on-insulator (SOI) structure, including a single crystal layer of silicon, comprising:
    a sensor formed with the single crystal silicon layer of the SOI structure for sensing temperature and light, the sensor generating a data signal in response to the temperature of the active matrix and the light transmittance of the liquid crystal material;
    a measurer for measuring the data signal from the sensor and generating a feedback signal in response to the data signal;
    an amplifier coupled to the gray-scale video signal and the measurer, a gain of the amplifier being responsive to the feedback signal, the amplifier amplifying the video signal by the gain which is dependent on at least one property of the liquid crystal.

18. The control apparatus of claim 17 wherein the sensor comprises at least one real-time light sensor and at least one real-time temperature sensor.

19. The control apparatus of claim 18 further comprising at least one light sensor generating a signal representing the light transmittance through a black pixel and at least one light sensor generating a signal representing the light transmittance through a white pixel.

20. The control of apparatus of claim 17 wherein the amplifier gain is nonlinear.

21. A control apparatus for driving an active matrix liquid crystal display in response to a stream of video signals from a video source, the display having an array of pixel transistors in between a substrate and an opposing substrate, the array being in a single crystal silicon layer of a silicon-on-insulator (SOI) structure, the pixel transistors addressed by a plurality of row lines and column lines, the apparatus comprising:
    an adhesive layer bonding the single crystal silicon layer to a substrate;
    a first select scanner and a second select scanner in the single crystal silicon layer and coupled to the video source and the row lines for addressing a select row of pixel transistors, each select scanner coupled to each row line at opposite sides of the active matrix region with each select scanner generating a simultaneous drive signal on the selected row line wherein each pixel transistor on the selected row line receives a portion of the drive signal from each select scanner;
    a data scanner in the single crystal silicon layer and coupled to the video source and the column line for driving the pixel transistors on the select row of pixel transistors in response to the video signals; and
    a temperature sensor formed with the single crystal layer between the substrate and the opposing substrate for sensing the temperature of the active matrix liquid crystal display.

22. The control apparatus of claim 21 further comprising a video polarity circuit in the SOI layer and coupled to the video source and the data scanner for generating an intensity signal for actuating the pixels in response to the video signals, the polarity of the intensity signal being reversed at a periodic rate.

23. The control apparatus of claim 22 wherein the periodic rate is once every video frame.

24. The control apparatus of claim 22 wherein the video polarity circuit generates an odd column intensity signal and an even column intensity signal for driving alternate columns of pixels with reversed polarity intensity signals.

25. The control apparatus of claim 21 further comprising a temperature measurer coupled to the temperature sensor for generating a temperature feedback signal to modify the video signal in response to the temperature of the active matrix region.

26. The control apparatus of claim 21 further comprising a light sensor disposed between the substrate and the opposing substrate for signaling relative light transmission changes through the liquid crystal.

27. The control apparatus of claim 26 further comprising a light meter coupled to the light sensor for generating a light feedback signal to modify the video signal in response to the light transmission change.

28. The control apparatus of claim 21 wherein the select scanners comprise respective shift registers, the shift registers being shifted to sequentially address a select row line.

29. The control apparatus of claim 21 wherein the active matrix region includes an array of pixel electrodes registered to the array of pixel transistors, wherein the pixel electrodes are patterned to reduce transmission loss through the pixel electrode.

30. The control apparatus of claim 29 wherein the pixel electrode pattern is a grid pattern.

31. The control apparatus of claim 30 wherein the patterned pixel electrode is at least one strip of semiconductor material having a wide of about 3 microns.

32. A control apparatus for driving an active matrix liquid crystal display in response to a stream of video signals from a video source, the display having an array of pixel transistors between a first substrate and a second substrate, the array being addressed by a plurality of row lines and a plurality of column lines, the apparatus comprising:
    an adhesive layer bonding a semiconductor device layer to a substrate, the device layer including the liquid crystal between the first substrate and the second substrate;
    a row driver;
    a column driver; and
    a temperature sensor between the first and the second substrates for sensing the temperature of the active matrix liquid crystal display.

33. The control apparatus of claim 32 further comprising a temperature measurer coupled to the temperature sensor for generating a temperature feedback signal to adjust the intensity signal in response to the temperature data.

34. The control apparatus of claim 26 further comprising a video polarity circuitry coupled to the temperature measurer and comprises an amplifier, a gain of the amplifier being responsive to the temperature feedback signal.

35. The control apparatus of claim 32 further comprising at least one light sensor disposed between the first substrate and the second substrate for signaling relative light transmission changes through the liquid crystal and a light meter coupled to the light sensor for generating a light feedback signal to adjust the intensity signal in response to the light transmission change.

36. A control apparatus for adjusting a gray-scale video signal of an active matrix liquid crystal display panel, the panel having an active matrix layer fabricated with a single crystal layer of silicon of a silicon-on-insulator (SOI) structure, comprising:
    a sensor formed with the single crystal silicon layer of the SOI structure that senses a property of the liquid crystal, the sensor generating a data signal in response to the property of the liquid crystal material;

a temperature measuring circuit that receives the data signal from the sensor and generates a feedback signal in response to the data signal; and an amplifier coupled to the gray-scale video signal and the measuring circuit, a gain of the amplifier being responsive to the feedback signal, the amplifier amplifying the video signal by the gain.

37. The control apparatus of claim 36 wherein the sensor comprises at least one real-time temperature sensor.

38. The control apparatus of claim 36 wherein the sensor comprises at least one light sensor generating a signal representing the light transmittance through a black pixel and at least one light sensor generating a signal representing the light transmittance through a white pixel.

* * * * *